United States Patent [19]
Barker

[11] 3,947,474
[45] Mar. 30, 1976

[54] CATALYST AND USE THEREOF
[75] Inventor: Robert S. Barker, Bloomfield, N.J.
[73] Assignee: Halcon International, Inc., New York, N.Y.
[22] Filed: Jan. 15, 1974
[21] Appl. No.: 433,602

Related U.S. Application Data
[60] Division of Ser. No. 300,026, Oct. 24, 1972, Pat. No. 3,838,067, which is a continuation-in-part of Ser. No. 76,249, Sept. 28, 1970, Pat. No. 3,759,840.

[52] U.S. Cl. .......................................... 260/346.8 A
[51] Int. Cl.$^2$ ....................................... C07D 307/60
[58] Field of Search .................. 260/346.8; 252/432

[56] References Cited
FOREIGN PATENTS OR APPLICATIONS
1,965,401   4/1971   Germany ......................... 260/346.8

*Primary Examiner*—Harry I. Moatz
*Attorney, Agent, or Firm*—William C. Long; David Dick; Riggs T. Stewart

[57] ABSTRACT

A catalyst useful for the oxidation of organic compounds, particularly vapor-phase oxidation of benzene with molecular oxygen to produce maleic anhydride, comprises the oxides of molybdenum, vanadium, phosphorus, sodium and boron in combination with an oxide of at least one metal of the group consisting of manganese, tin, tungsten and bismuth, and preferably also in combination with an oxide of at least one member of the group consisting of iron, cobalt and nickel.

3 Claims, No Drawings

CATALYST AND USE THEREOF

CROSS-REFERENCE TO RELATED APPLICATION

This is a division of application Ser. No. 300,026, filed Oct. 24, 1972 (now U.S. Pat. No. 3,838,067) which in turn is a continuation-in-part of application Ser. No. 76,249, filed Sept. 28, 1970 (now U.S. Pat. No. 3,759,840)

This invention relates to catalysts and is more particularly concerned with catalysts which are useful in the oxidation of organic compounds, especially vapor-phase oxidation of benzene with molecular oxygen to produce maleic anhydride. The invention is also concerned with the use of such catalysts in oxidations of this character.

The preparation of maleic anhydride by the selective partial oxidation of benzene in a vapor phase system using a contact catalyst involves a well-known reaction and has been practiced commercially for many years. Among catalysts which have been found useful and effective commercially for this purpose are those based upon a combination of vanadium and molybdenum in oxidized form. In the development of improved catalysts of this nature the vanadium and molybdenum oxides have been combined with the oxidized forms of one or more other metals of various types.

Known commercial catalysts of this character are effective and generally satisfactory, but in the field of catalysis there is always a continuing search for improved catalyst compositions, and a particular objective is the discovery of means for providing high activity of the catalysts while at the same time enhancing, or at least maintaining, the selectivity of the catalyst in favor of the desired product. Of particular interest to persons skilled in this art is the development of catalysts which are effective at lower oxidation temperatures and which have an increased active life. There are obvious important practical benefits in a catalyst which is active and retains its activity for a long period of time before it needs to be replaced.

It is accordingly an object of this invention to provide an improved catalyst of the vanadium oxide-molybdenum oxide type which is effective at lower temperatures and has an increased active life.

It is a further objective of the invention to provide a catalyst for the character indicated which has desirable activity and selectivity characteristics.

It is a more specific object of the invention to provide a catalyst which has an increased active life and has high activity and selectivity with respect to the production of maleic anhydride by the oxidation of benzene.

Another object of the invention is to provide an improved method for the catalytic oxidation of benzene to produce maleic anhydride which employs a catalyst of the type described.

In accordance with the invention, it has been discovered that the combination, in a catalyst of the vanadium oxide-molybdenum oxide type which includes an oxide of phosphorus, sodium and boron, and preferably also an oxide of at least one member of the group consisting of iron, cobalt, and nickel, of a small amount of an oxide of at least one member of the group consisting of manganese, tin, tungsten, and bismuth, provides a catalyst having an increased active life and having desirable activity and selectivity in the production of maleic anhydride by the oxidation of benzene. An especially important feature of the catalyst of this invention is its effectiveness at relatively low oxidation temperatures, e.g. jacket temperatures in the range of 340°C. to 360°C. Of course, higher temperatures can also be used.

The basic catalyst system comprising the combination of oxides of vanadium, molybdenum, phosphorus, sodium and boron and preferably also including an oxide of iron, cobalt and nickel is disclosed in my co-pending application Ser. No. 76,249, filed Sept. 28, 1970, now U.S. Pat. No. 3,759,840. In accordance with the present invention, improved results are achieved by combining that basic catalyst system with an oxide of at least one member of the group consisting of manganese, tin, tungsten and bismuth, and it is preferred to combine the oxide of manganese, tin tungsten or bismuth with the preferred basic catalyst system of the co-pending application, i.e. the system including an oxide of iron, cobalt or nickel. It is especially preferred to use the combination of two or more of the oxides of manganese, tin, tungsten or bismuth.

In the catalyst composition of the invention, all of the elements mentioned are considered to be in the form of their oxides, e.g. $V_2O_5$, $MoO_3$, $P_2O_5$, $Na_2O$, $Co_2O_3$, $Ni_2O_3$, $Fe_2O_3$, $B_2O_3$, $MnO$, $SnO_2$, $WO_2$ and $Bi_2O_3$, since the catalyst is advantageously prepared by means of known techniques which involve "activation" by a prolonged heat treatment as a concluding step. However, it is convenient to refer to the proportions of the various components in terms of the elements themselves. In this way, the catalyst of the invention can be characterized by its analytical composition in which the components are expressed in meaningful terms without regard to the exact chemical composition or form in which they may actually exist. Thus, basing the proportions on a molar quantity of vanadium as 1.0, the molybdenum may be in the range of 0.1 to 0.95 mol, the phosphorus content may be in the range of 0.01 to 0.5 mol, the alkali metal content may be in the range of 0.02 to 0.6 mol, the boron may be in the range of 0.005 to 0.3 mol, the content of the Co, Ni, or Fe may be in the range of 0.005 to 0.10 mol and the Mn, Sn, W or Bi may be in the range of 0.005 to 0.1 mol.

As is customary in the case of vanadium oxide-molybdenum oxide oxidation catalysts, the active catalytic components are desirably supported upon a suitable carrier, generally in the form of refractory inorganic particles, of any of the various catalyst supports known to this art, conventionally characterized as inert, having a surface area of at most 5 square meters per gram, e.g. 0.002 to 5 square meters per gram, preferably 0.005 to 3 square meters per gram, and of a particle size adapted for the particular process in which the catalyst is to be used. Generally suitable are particles having an average diameter of about 1/5–½ inch, although larger or smaller particle sizes can also be employed, e.g. average diameters of ⅛ to ¾ inch.

The weight of catalyst mixture relative to the support may be in the range of 1.0 to 20%, preferably about 10% based on the weight of the support. Although alumina is a preferred support, other refractory support materials may be used, such as silicon carbide, silica, titania, fuller's earth, pumice, asbestos, kieselguhr, and the like. The carrier material may be in the form of pellets, lumps, granules, spheres, rings or other formed pieces, or in other forms which may be of regular or irregular contour.

It is appreciated that manganese, tin, tungsten, and bismuth have been proposed as catalyst components, for example in Slotterbeck et al. U.S. Pat. No. 2,260,409 and in Bethell et. al. U.S. Pat. No. 3,435,069 but such catalysts involve the use of these components in systems and environments which are basically different from the catalyst compositions of the present invention which have improved characteristics.

When the catalyst of this invention is used in the vapor-phase oxidation of benzene to form maleic anhydride, the oxidation conditions employed are those generally associated with this reaction, as disclosed, for example, in Egbert and Becker, U.S. Pat. No. 2,777,860 and Egbert U.S. Pat. No. 3,211,671. Typical conditions involve jacket temperatures of 340° to 420°C., a ratio of benzene to molecular oxygen: 1–1.6 to 20 (mol) and a space velocity of 2000 to 4000 hour$^{-1}$, and pressures of atmospheric to 3 atm. Similarly, conventional reactors or converters can be employed and the processes in which the catalyst of the invention can be used are, therefore, not restricted to particular conditions or types of apparatus. However, it is one of the features of the catalyst of this invention that the oxidation of benzene to maleic anhydride can be carried out at lower temperatures, e.g. in the 340°–370°C. range, than would normally be employed with conventional catalysts, all other conditions being the same.

As mentioned, the catalyst is suitably prepared by more or less conventional techniques. In a preferred precedure, for example, the molybdenum, in the form of ammonium molybdate, is dissolved in concentrated aqueous HCl (35%), and a mixture of a hydrated disodium acid phosphate, and boron, in the form of a hydrated sodium tetraborate, are dissolved in hot water and added to the acidic solution. Ammonium metavanadate is dissolved in a second batch of concentrated HCl and the Mn, Sn, W or Bi value is added to the ammonium metavanadate solution in the form of a chloride, nitrate or other salt dissolved in a small amount of water. When more than one member of the Mn, Sn, W and Bi additive group is to be incorporated, it is preferred to add them separately or consecutively. If, in accordance with the preferred form of the invention, Co, Ni and/or Fe are to be incorporated, a water-soluble salt of the metal, e.g. cobalt nitrate hexahydrate, is dissolved in water and the resulting aqueous solution is added to the ammonium metavanadate solution. Finally, the two HCl solutions are then mixed by slowly adding the molybdate solution to the metavanadate solution and the combined solution is mixed with particles of a suitable refractory carrier and evaporated, resulting in the disposition of the salts on the surface in the pores of the carrier. The coated carrier particles are then activated by calcining them in a kiln or oven, or in a tube through which air is passed, at an elevated temperature (e.g. 175°–400°C.) for ½ to 2 hours. Since the preferred form of the catalyst of this invention is related to the catalyst disclosed in U.S. Pat. Nos. 2,777,860 and 3,211,671, the catalyst preparation methods disclosed in those patents, with the further addition of the boron compound and the Mn, Sn, W and/or Bi compound are suitably employed. In the catalyst of the present invention it is particularly preferred to use Mn, Sn or W values, or mixtures of them.

While, as mentioned, the invention in its broadest sense is not limited to a particular carrier material, a support is preferred which has an apparent porosity (pore volume) or at least 35%, a surface area (square meters per gram) of about 0.01 to about 1, and a major pore diameter range of 50 to 1500 microns, preferably at least 80% of 50 to 1500 micron size. An alumina support having these characteristics is preferred, especially an alumina-silica support containing up to about 20% silica, the balance being substantially alumina. Particularly good results are obtained with a support of the character indicated which has an apparent porosity of at least 50%, and a pore diameter range of at least 95% of 50–1500 micron size.

The features of the invention will be more readily apparent from the following specific examples of typical application. It will be understood, however, that these examples are for the purpose of illustration only and are not to be interpreted as limiting the invention.

EXAMPLE I

A first solution (A) is prepared by dissolving 175 g. ammonium metavanadate slowly with stirring in 500 ml. of conc. hydrochloric acid (sp. g. 1.19) followed by the addition of 9.8 g. manganese nitrate in the form of a 50% solution in water (25°C.). A second solution (B) is prepared by dissolving 100 g. of ammonium paramolybdate in 500 ml. of conc. hydrochloric acid, and 3 g. sodium tungstate in 10 ml. hot water (75°C.) is added to the solution with stirring, followed by the addition of a mixture of 10.5 g. disodium acid phosphate dodecahydrate and 9.6 g. sodium borate pentahydrate dissolved in 75 ml. hot water (70°C.). Solution B is then slowly added to solution A with stirring and the resultant mixture poured over 1500 ml. of 3–5 mesh aggregate pellets of a commercial alumina catalyst carrier composed of about 85% $Al_2O_3$, about 13.5% $SiO_2$, and very small amounts of other oxides as impurities, primarily alkali metal oxides and alkaline earth metal oxides. This carrier has an apparent porosity of about 55–60%, a surface area of about 0.1 sq. meters per gram and a pore diameter range of about 95% of 50–1500 micron size. The mixture is heated in a rotating glass jar to evaporate the solution to dryness, leaving a greenish coated product which is then placed in an activation oven for 4 hours at 400°C. to activate it, the additive elements thereby being converted into their oxides. In similar manner, there are prepared a series of other catalysts, supported on the alumina carrier, each containing a combination of vanadium, molybdenum, phosphorus, sodium, and boron with manganese, tin, tungsten and/or bismuth, and in some cases with nickel, cobalt, and/or iron, within the scope of the formulation set forth above, but formed from varying quantities of precursor salts or employing different precursor salts.

In order to evaluate the foregoing catalysts, each is used to form a catalyst bed in a series of runs wherein benzene is oxidized by means of molecular oxygen to maleic anhydride. For this purpose, each catalyst is charged into a vertical reactor tube of 0.9 inch internal diameter, to a bed height of 120 inches, surrounded with a temperature regulating medium such as salt contained in a heating jacket. A benzene-air mixture is fed downwardly through the reactor at a linear velocity of one foot per 0.1 second calculated at reaction conditions. The feed mixture contains 1.4 mol percent of benzene in air, and the jacket temperature is maintained in the range of 350° to 370°C. The product is recovered in known manner. The results obtained with each of the catalysts are shown in the following table wherein catalyst No. 1 is the catalyst prepared in the manner described at the beginning of this example.

Catalyst No. 2 is like catalyst No. 1, except that iron nitrate, 9 g., is substituted for the tungstate. Catalyst No. 3 is like catalyst No. 1, except that iron nitrate, 9 g., and sodium stannate, 3 g., is substituted for the tungstate. Catalyst No. 4 is formed from the components in catalyst No. 1, except that iron nitrate, 10 g., is substituted for the manganese. Catalyst No. 5 is formed from the components in catalyst No. 1, except that cobalt nitrate, 9 g., is substituted for the manganese. Catalyst No. 6 is the same as catalyst No. 5 except that 3 g. of sodium stannate is substituted for the tungstate. Catalyst No. 7 is like catalyst No. 1 but 10 g. of bismuth nitrate is substituted for the tungstate.

TABLE I

| Catalyst | Temperature °C. | Selectivity Mol % | Conversion, Wt.% | Yield, Wt.% |
|---|---|---|---|---|
| 1 | 360 | 74.5 | 98 | 92 |
| 2 | 350 | 75 | 99 | 93 |
| 3 | 365 | 75 | 99 | 93 |
| 4 | 358 | 75 | 97 | 93 |
| 5 | 360 | 75 | 97 | 93 |
| 6 | 365 | 75 | 97 | 93 |
| 7 | 370 | 74.5 | 99 | 93 |

As pointed out above, one of the characteristics of the catalyst of this invention is prolonged active life. This is clearly demonstrated by comparing a typical catalyst in accordance with the invention which is characterized by a small but effective content of manganese, tin, tungsten and/or bismuth with an analogous catalyst which is free from any of these four additives, in the actual vapor-phase partial oxidation of benzene to maleic anhydride in an accelerated testing system in which the effect of several months of operation can be reduced to a matter of hours. In the accelerated test, the operating conditions observed correspond to those described in Example I, except that a temperature of 380°C. and 400°C. is used, but the temperature is reduced to 360°C. at repeated intervals to measure the activity (conversion) at the latter temperature.

Using this accelerated method, it is found that in a typical case, a catalyst in accordance with this invention, e.g. corresponding to catalyst No. 3 described above, exhibits a significantly increased active life which is at least twice as long in comparison with an analogous catalyst having no content of Mn, Sn, W or Bi.

The embodiments of the invention in which an exclusive property is claimed are defined as follows:

1. A process for the preparation of maleic anhydride which comprises oxidizing benzene in the vapor-phase with molecular oxygen in the oxygen in the presence of a catalyst consisting essentially of oxides of molybdenum, vanadium, phosphorus, sodium and boron in combination with an oxide of at least one metal selected from the group consisting of manganese, tin, tungsten and bismuth, the relative amounts of said oxides expressed as Mo, V, P, Na, B, Mn, Sn, W and Bi, being per mol of V, 0.1 to 95 mol Mo, 0.01 to 0.5 mol P, 0.02 to 0.6 mol Na, 0.005 to 0.3 mol B, 0.005 to 0.1 mol Mn, 0.005 to 0.1 mol Sn, 0.005 to 0.1 mol W, and 0.005 to 0.1 mol Bi.

2. A process as defined in claim 1, wherein said catalyst further contains 0.005 to 0.1 mol of an oxide of at least one member of the group consisting of cobalt, nickel or iron.

3. A process for the preparation of maleic anhydride which comprises oxidizing benzene in the vapor-phase with molecular oxygen in the presence of a molybdenum oxide-vanadium oxide-phosphorus oxide-sodium oxide-boron oxide catalyst wherein said molybdenum oxide, vanadium oxide, phosphorus oxide, sodium oxide and boron oxide, expressed as Mo, V, P, Na and B, are present per mol of V in the amount of 0.1 to 0.95 mol Mo, 0.01 to 0.5 mol P, 0.02 to 0.6 mol Na and 0.005 to 0.3 mol B, and in combination with said catalyst a small amount of an oxide of at least one metal selected from the group consisting of manganese, tin, tungsten and bismuth, effective to prolong the active life of said catalyst.

* * * * *

UNITED STATES PATENT OFFICE
CERTIFICATE OF CORRECTION

PATENT NO. : 3,947,474
DATED : March 30, 1976
INVENTOR(S) : Robert S. Barker

It is certified that error appears in the above-identified patent and that said Letters Patent are hereby corrected as shown below:

Col. 3, line 52, after "surface" insert -- and --

Col. 3, line 67, change "or" to -- of --

Signed and Sealed this

Twelfth Day of April 1977

[SEAL]

Attest:

RUTH C. MASON
Attesting Officer

C. MARSHALL DANN
Commissioner of Patents and Trademarks